US012071723B2

(12) United States Patent
Youssef et al.

(10) Patent No.: US 12,071,723 B2
(45) Date of Patent: Aug. 27, 2024

(54) SMELT SHATTERING METHOD AND APPARATUS

(71) Applicant: The Babcock & Wilcox Company, Akron, OH (US)

(72) Inventors: Simon F. Youssef, Lancaster, OH (US); Tony F. Habib, Lancaster, OH (US); Stephen L Shover, Millersport, OH (US)

(73) Assignee: The Babcock & Wilcox Company, Akron, OH (US)

( * ) Notice: Subject to any disclaimer, the term of this patent is extended or adjusted under 35 U.S.C. 154(b) by 251 days.

(21) Appl. No.: 17/470,618

(22) Filed: Sep. 9, 2021

(65) Prior Publication Data

US 2022/0074142 A1 Mar. 10, 2022

Related U.S. Application Data

(60) Provisional application No. 63/076,665, filed on Sep. 10, 2020.

(51) Int. Cl.
*D21C 11/12* (2006.01)
*A61M 1/00* (2006.01)
*D21C 11/00* (2006.01)

(52) U.S. Cl.
CPC .......... *D21C 11/122* (2013.01); *A61M 1/804* (2021.05); *D21C 11/0078* (2013.01)

(58) Field of Classification Search
CPC ..... D21C 11/12; D21C 11/0078; A61M 1/804
See application file for complete search history.

(56) References Cited

U.S. PATENT DOCUMENTS

| 3,184,916 | A  | * | 5/1965  | Ravel  | F02K 9/978 |
|   |   |   |   |   | 239/266 |
| 2008/0290193 | A1 | * | 11/2008 | Hursen | B05B 1/005 |
|   |   |   |   |   | 239/455 |
| 2010/0102139 | A1 | * | 4/2010  | Hursen | B24C 7/0046 |
|   |   |   |   |   | 239/11 |

FOREIGN PATENT DOCUMENTS

| CN | 113741557 | A | * | 12/2021 |  |
| DE | 102019135375 | A1 | * | 6/2021 | B23K 26/14 |

OTHER PUBLICATIONS

Taranenko, Shattering Kraft Recovery Boiler Smelt by a Steam Jet, 2013, University of Toronto. (Year: 2013).*

(Continued)

*Primary Examiner* — Anthony Calandra
(74) *Attorney, Agent, or Firm* — Michael J. Seymour (57) ABSTRACT

A smelt shattering apparatus includes an inlet orifice, an outlet orifice, and a fluidic pathway between the inlet orifice and the outlet orifice. A convergence divergence zone is located between the inlet orifice and the outlet orifice. In one illustrative construction, a first separable section includes the inlet orifice, and a second separable section includes the outlet orifice and a divergence zone of the convergence divergence zone. In some constructions, there may be a second outlet orifice in fluidic communication with the inlet orifice. To provide uniformity over the multiple shatter jets, the first outlet orifice may have a cross-sectional dimension and the second outlet orifice is located a distance of between about 4 and about 10 times of the cross-sectional dimension from the first outlet orifice.

12 Claims, 13 Drawing Sheets

(56) References Cited

OTHER PUBLICATIONS

Jin et al., Development of converging-diverging multi-jet nozzles for molten smelt shattering in kraft recovery boiler, Mar. 2021, TAPPI, vol. 20 No.3 (Year: 2021).*

Taranenko et al., A laboratory study of recovery boiler smelt shattering, Aug. 2014, TAPPI Journal, vol. 13 No.8 (Year: 2014).*

CN113741557A English translation, 2020. (Year: 2020).*

\* cited by examiner

SMELT SHATTERING METHOD AND APPARATUS

This application claims the benefit of U.S. Provisional Application No. 63/076,665 filed Sep. 10, 2020 and titled "SMELT SHATTERING METHOD AND APPARATUS". U.S. Provisional Application No. 63/076,665 filed Sep. 10, 2020 and titled "SMELT SHATTERING METHOD AND APPARATUS" is incorporated herein by reference in its entirety.

FIELD OF THE INVENTION

This invention relates to smelt processing, to Kraft wood pulping processes, to Kraft wood pulping mills, to black liquor recovery processes and apparatuses, and to related fields.

BACKGROUND OF THE INVENTION

Conversion of wood into wood pulp is typically done using the Kraft process. Wood chips are cooked in a mixture containing water, sodium hydroxide, and sodium sulfide. This mixture, commonly referred to as white liquor, assists with separating the cellulose fibers (wood pulp) from the lignin holding the fibers together. The separated cellulose fiber are then removed, leaving behind a waste product, typically referred to as black liquor.

Reclamation and reuse of the cooking chemicals from the black liquor is desirable to control costs associated with the paper-making process. During the recovery process, the black liquor is concentrated into a solution containing approximately 65 to 80 percent solids. The concentrated solution is sprayed into the internal volume of a chemical reduction furnace, also sometimes referred to as a recovery boiler. The black liquor is burned in the recovery boiler to recover the spent pulping chemicals and to produce steam and power for use in various processes. The combustion results in the formation of a molten smelt pool at the bottom of the boiler primarily consisting of sodium carbonate ($Na_2CO_3$) and sodium sulfide ($Na_2S$). Molten smelt having a density of about 2000 kg/m³ and a surface tension of about 0.21 N/m continuously flows out of the boiler at about 780 to 830° C. (1440 to 1530° F.) through several spouts at a flow rate of about 1 l/s per spout. Preferably, the smelt streams are broken up by a shatter jet into small droplets of a few millimeters.

The shattered smelt droplets fall into a dissolving tank where they dissolve in a weak wash (water recycled from the causticizing plant) to form a green liquor. The interaction between molten smelt and green liquor can be loud and violent. In extreme cases, dissolving tank explosions occur and may cause equipment damage, personnel injuries, and boiler shutdowns. These extreme cases are undesirable, prompting increasingly stringent regulations. Development of new and improved smelt nozzles and methods for effective and safe dissolving tank operation are a top priority in pulp mill operation.

Certain improvements are disclosed herein.

BRIEF SUMMARY

In some illustrative embodiments disclosed herein as nonlimiting examples, a smelt shattering apparatus comprises an inlet orifice, an outlet orifice, a fluidic pathway between the inlet orifice and the outlet orifice, and a convergence divergence zone located between the inlet orifice and the outlet orifice. In some such embodiments, a first separable section includes the inlet orifice, and a second separable section includes the outlet orifice and a divergence zone of the convergence divergence zone. In some embodiments, there may be a second outlet orifice in fluidic communication with the inlet orifice. In some such embodiments, the first outlet orifice may have a cross-sectional dimension and the second outlet orifice is located a distance of between about 4 and about 10 times of the cross-sectional dimension from the first outlet orifice.

In some illustrative embodiments disclosed herein as nonlimiting examples, a smelt shattering nozzle comprises an inlet orifice, an outlet orifice, and a fluidic pathway between the inlet orifice and the outlet orifice having a constriction. In some such embodiments, the nozzle comprises a first section including the inlet orifice, and a second section including the outlet orifice, with the first section and the second section secured together to define the fluidic pathway with the constriction defined at an interface between the first and second sections. In some such embodiments, the portion of the fluidic pathway in the second section widens from the interface to the outlet orifice. In some such embodiments, the portion of the fluidic pathway in the first section has a larger diameter than the portion of the fluidic pathway in the second section. In some embodiments the portion of the fluidic pathway extending from the inlet orifice to the constriction narrows leading into the constriction.

In some illustrative embodiments disclosed herein as nonlimiting examples, a smelt shattering apparatus comprises a plurality of smelt shattering nozzles as set forth in the immediately preceding paragraph. The outlet orifices of the smelt shattering nozzles have a diameter, and a spacing between the outlet orifices of the plurality of smelt shattering nozzles is less than or equal to eight times the diameter.

In some illustrative embodiments disclosed herein as nonlimiting examples, a method is disclosed of smelt shattering. A smelt shattering apparatus is provided, including an inlet orifice, an outlet orifice, a fluidic pathway between the inlet orifice and the outlet orifice, and a convergence divergence zone located between the inlet orifice and the outlet orifice. A fluidic stream is flowed thru the fluidic pathway to produce a fluidic jet. The fluidic jet is contacted with a smelt stream to convert the smelt stream to shattered smelt. The shattered smelt is disposed in a dissolving tank. In some embodiments, the fluidic stream comprises steam. In some embodiments, the method further includes producing the smelt stream using a Kraft pulp mill by burning black liquor in a recovery boiler.

DETAILED DESCRIPTION OF THE INVENTION

Figure 1:
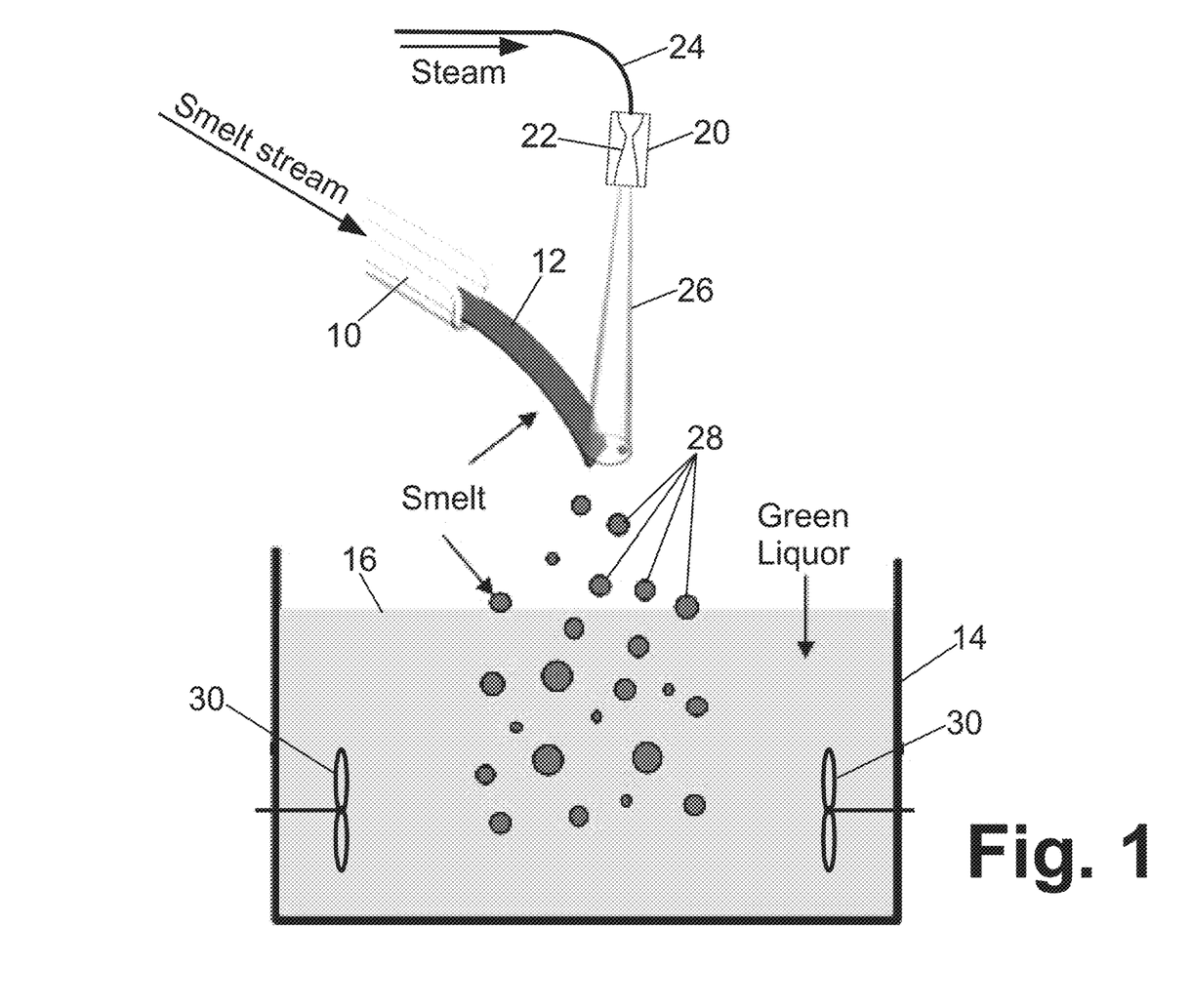
FIG. 1 diagrammatically illustrates a smelt shattering apparatus feeding into a dissolving tank.

With reference to FIG. 1, a smelt shattering apparatus feeding into a dissolving tank is shown. A smelt stream is produced using a Kraft pulp mill by burning black liquor in a recovery boiler (not shown). A smelt nozzle 10 delivers a smelt stream 12 to a dissolving tank 14 containing a solvent fluid such as water (e.g., a weak wash comprising water recycled from a causticizing plant) to form a green liquor 16. A shatter jet nozzle 20 (shown in sectional view in FIG. 1 to reveal an internal fluidic pathway 22) receives a fluidic stream 24, such as illustrative steam 24 which flows thru the fluidic pathway 22 to produce a fluidic jet 26 that contacts with the smelt stream 12 to convert the smelt stream 12 to shattered smelt 28 which is then disposed in the dissolving tank 14. Optionally, the dissolving tank may include impellers 30 or the like to circulate the green liquor 16 to assist in the processing of the shattered smelt 28.

Numerous studies have been conducted on dissolving tank safety. The results have shown that molten smelt droplets often do not explode immediately when they meet water, but rather, remain stable in water for a few seconds before they explode. It was further observed that the explosion of one droplet may trigger the explosions of other droplets nearby, leading to a chain of multi-droplet explosions. These findings imply that 1) droplet-scale or "mini" smelt-water explosions are needed for effective smelt dissolution in the dissolving tank, and 2) large-scale explosions caused by either one large piece of molten smelt or many small droplets in a small, confined area can be violent.

Figure 2:
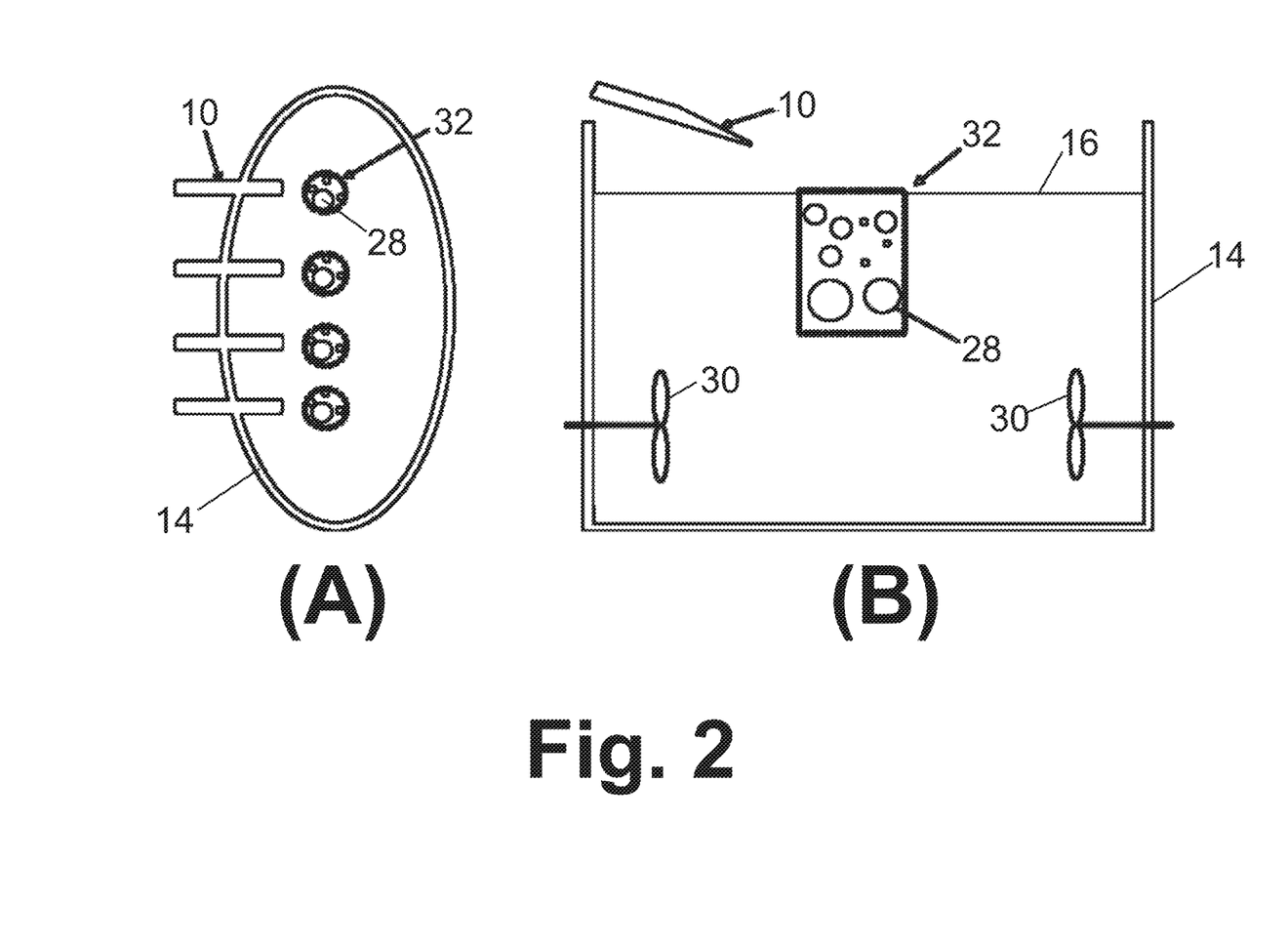
FIG. 2 diagrammatically illustrates (A) a top view and (B) a side view of shattered smelt entering a dissolving tank.

FIG. 2 diagrammatically depicts the interaction between smelt from the smelt spout 10 and water in the dissolving tank 14 from (A) top and (B) side views. The distribution of smelt droplets (i.e., droplets of the shattered smelt 28) and the projected area in which the droplets continuously fall into are greatly affected by the smelt shattering. As the droplets reach and continue to sink in the liquor, they form a cylindrical volume 32 of smelt-green liquor mixture (diagrammatically shown as a rectangular box in FIG. 2 part A, and as circles in FIG. 2 part B). The extreme-case scenario occurs when all the smelt droplets within the boundary of the control volume 32 explode at the same time.

A thermodynamic model, based on Hicks-Menzies principles was developed to calculate the energy released by a large smelt-water interaction in the dissolving tank. The results showed that the conversion ratio (CR), which is the ratio of the total explosion energy to the available thermal energy stored in the smelt, increases with increasing green liquor temperature and green liquor-to-smelt volume ratio. This implies that to reduce the probability of a dissolving tank explosion, the shatter jet design needs to be optimized so that molten smelt droplets can be uniformly distributed over a large area on the green liquor.

Smelt shatter jet designs and shattering practices vary widely from mill to mill with no clear guidelines in the industry for nozzle design, configuration, and operation. Typically, nozzles operate with saturated steam (3.5 to 15.5 bar, corresponding to 50 to 225 psig; and at 150 to 250° C., corresponding to 300 to 480° F.) and the resulting shatter jets are directed vertically downward or slightly against the direction of smelt flow.

Figure 3:
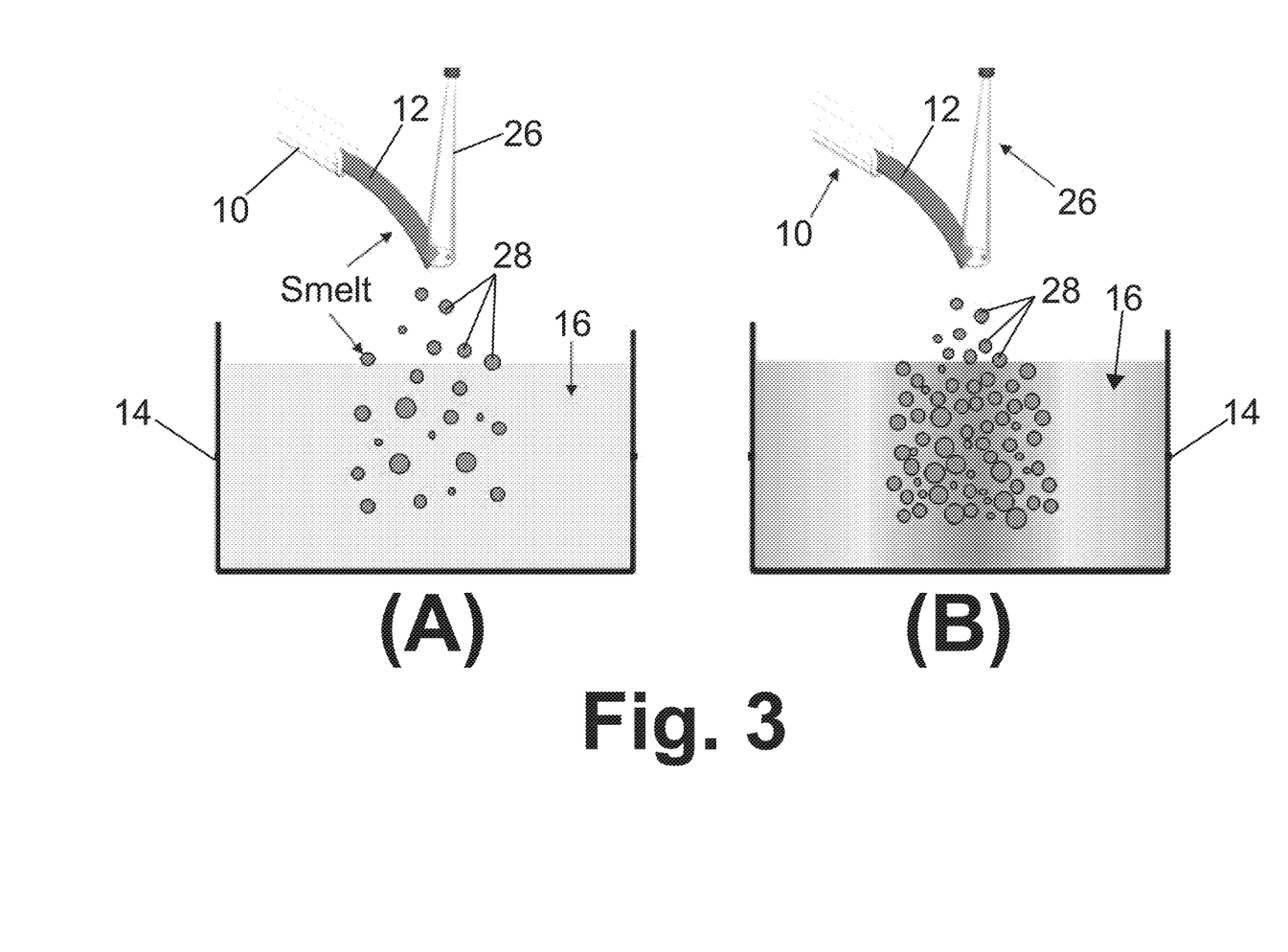
FIG. 3 diagrammatically illustrates smelt-water interaction in the case of (A) a low concentration of shattered smelt in the entry region of smelt into the tank and (B) a high concentration of shattered smelt in the entry region.

With reference to FIG. 3, smelt-water interaction is diagrammatically shown in the case of (A) a low concentration of shattered smelt 28 in the entry region of smelt into the green liquor 16 in the dissolving tank 14, and (B) a high concentration of shattered smelt 28 in the entry region. FIG. 3 also diagrammatically depicts the smelt spout 10, smelt stream 12, and shatter jet 26 as previously described with reference to FIG. 1. Dissolving tank operation upsets often occur when the smelt flow exceeds the capacity of shatter jets. Such overflow situations include smelt runoffs (a sudden increase in smelt flow) and "Jellyroll" smelt. Jellyroll smelt can be caused by either sudden freezing of molten smelt, fallen deposits, or inclusion of a large amount of unburned char. This slow-moving viscous smelt makes smelt 12 more difficult to shatter, and when it is removed, a surge of molten smelt behind it can lead to a runoff situation. When this occurs, the smelt flow overwhelms the capacity of the smelt shatter jet, making it ineffective. As a result, the molten smelt typically becomes concentrated in an area directly below the spout, as diagrammatically shown in FIG. 3(B), increasing the explosion energy. A shatter jet having sufficient shattering energy to handle both normal smelt flow and upset conditions is thus desirable.

In some cases a shatter jet 26 may miss a portion or all the smelt flow 12 due to a change in smelt flow characteristics. Thus, a shatter jet having wide coverage is also desirable. Further, while smelt shattering should attain optimum droplet distribution, there is also a desire to minimize steam consumption to reduce operating cost.

Thus, it is recognized herein that a shatter jet nozzle should desirably be capable of meeting multiple criteria: i) generating high shattering energy, ii) enabling wide coverage, and iii) minimizing steam consumption. Disclosed herein are embodiments of a shatter jet nozzle and methods of performing smelt shattering that address these multiple criteria, e.g. having sufficient shattering energy to handle both normal smelt flow and upset conditions, providing wide coverage, and minimizing steam consumption.

Figure 4:
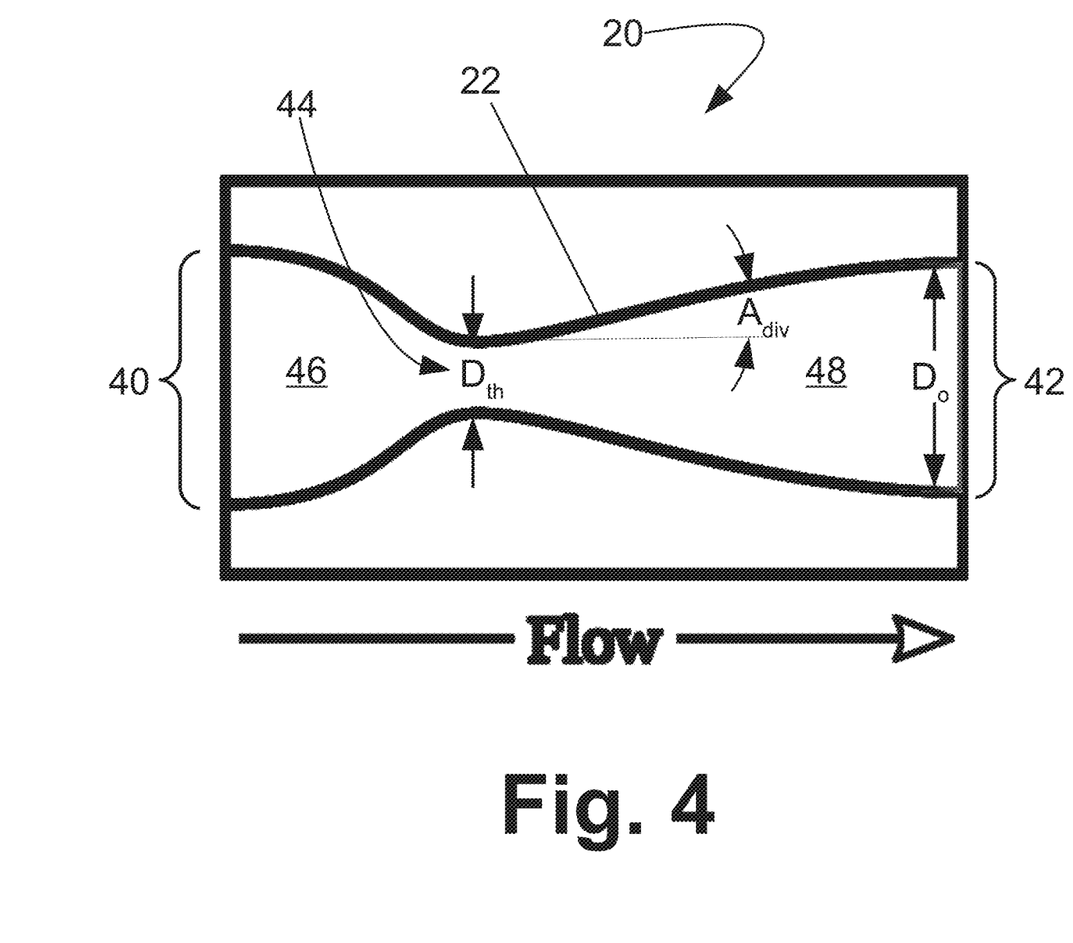
FIG. 4 diagrammatically illustrates an enlarged side-sectional view of the smelt shattering nozzle of FIG. 1.
Figure 5:
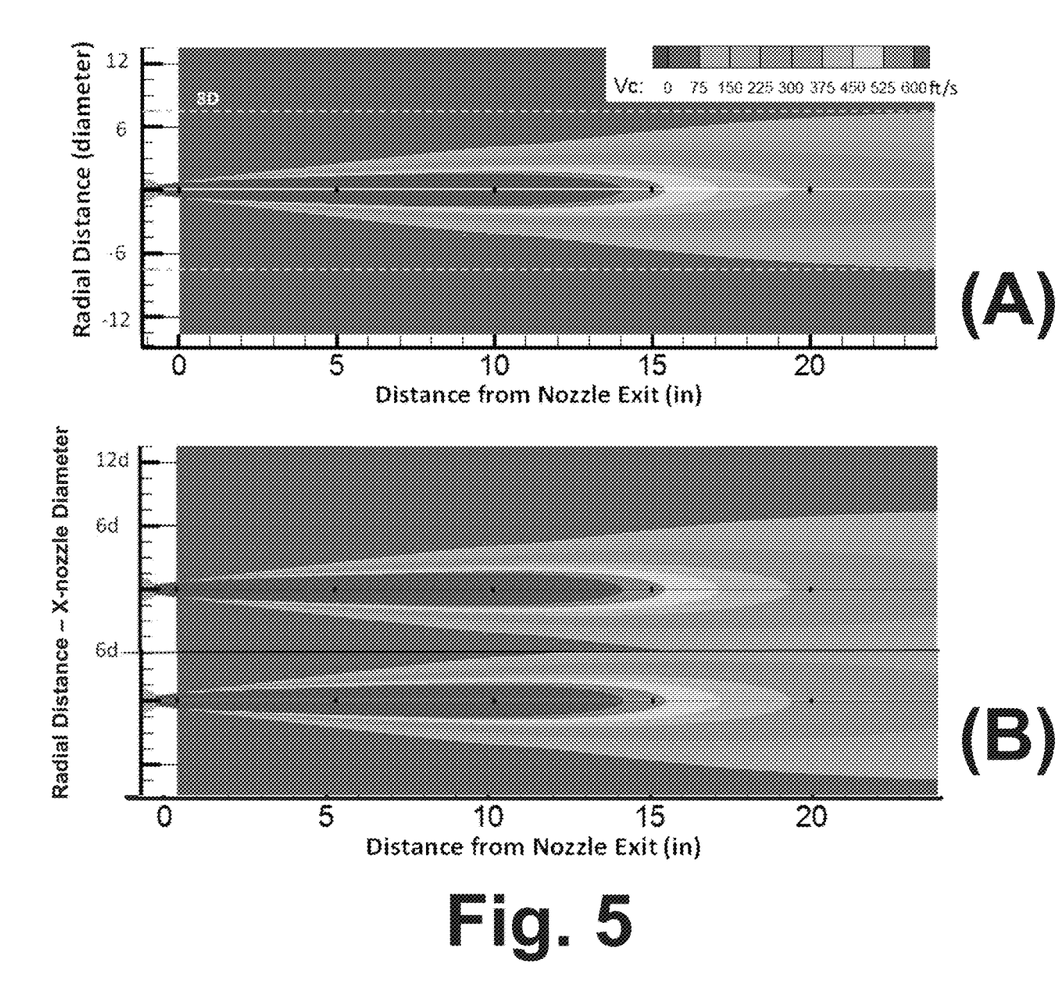
FIGS. 5-11 present various flow calculations as described herein.

With reference to FIG. 4, an enlarged side sectional view of the shatter jet nozzle 20 of FIG. 1 is shown. To improve shatter jet strength while minimizing steam consumption, the shatter jet nozzle 20 comprises a converging-diverging (CD) nozzle design. In the illustrative design, the shatter jet nozzle 20 includes an inlet orifice 40, an outlet orifice 42, and the internal fluidic pathway 22 between the inlet orifice 40 and the outlet orifice 42. The outlet orifice 42 has a cross-sectional dimension $D_o$ which is a diameter $D_o$ when the outlet orifice 42 has a circular cross-section. Flow of steam or other working fluid is from left-to-right in the orientation of the nozzle 20 shown in FIG. 1, as indicated by the "Flow" arrow. That is, the steam enters the inlet orifice 40, passes through the fluidic pathway 22, and exits the outlet orifice 42.

The fluidic pathway 22 has a constriction or throat 44 which divides the fluidic pathway 22 into a convergence zone 46 between the inlet orifice 40 to the throat 44 and a divergence zone 48 between the throat 44 to the outlet orifice 42. The terms "constriction" and "throat" are used interchangeably herein to refer to the narrowed portion of the fluidic pathway 22 separating the convergence zone 46 and the divergence zone 48. In general, the steam flows at a high pressure and low velocity in the convergence zone 46 as the steam converges into the constriction or throat 44; then the steam diverges as it exits the throat 44 so that the steam in the divergence zone 48 is at a lower pressure and higher velocity compared with the respective high pressure and low velocity in the convergence zone 46. The divergence zone 48 widens from the constriction or throat 44 to the outlet orifice 42. The convergence zone 46, that is, the portion of the fluidic pathway 22 extending from the inlet orifice 40 to the constriction 44, optionally narrows leading into the constriction 44, although it may in other embodiments be of constant inner lumen diameter (see, e.g. FIG. 13). The combination of the convergence zone 46, the constriction or throat 44, and the divergence zone 48 is sometimes referred to herein as a convergence divergence zone, which is located between the inlet orifice 40 and the outlet orifice 42. For the indicated flow of steam, the convergence zone 46 is upstream of the divergence zone 48; or, conversely, the divergence zone 48 is downstream of the convergence zone 46.

The complex fluid dynamics of the shatter jet nozzle 20 enable and allow the steam flow to reach sonic velocity at a throat or constriction 44 and higher at the exit, i.e. outlet orifice 42. Factors, including outlet diameter $D_o$, a throat diameter $D_{th}$ of the constriction or throat 44, an expansion angle $A_{div}$ of the divergence zone 48, and nozzle length, enable customization of the shatter jet nozzle 20 for use with various smelt flow characteristics.

A converging-diverging (CD) nozzle with a suitably designed throat-to-outlet orifice area ratio R:

$$R = \frac{\pi \left(\frac{D_{th}}{2}\right)^2}{\pi \left(\frac{D_o}{2}\right)^2} = \left(\frac{D_{th}}{D_o}\right)^2 \quad (1)$$

achieves higher impact pressure with the given steam flow than a cylindrical hole nozzle, due to its more effective jet expansion that achieves same strength at lesser steam consumption. The flow rate of a nozzle can be calculated by:

$$m = C_d A \sqrt{\gamma \rho_o P_o \left(\frac{2}{\gamma+1}\right)^{\frac{\gamma+1}{\gamma-1}}} \quad (2)$$

where m is the mass flow rate, $C_d$ is the discharge coefficient, A is the cross-sectional area of the choke point (i.e., $$A = \pi \left(\frac{D_{th}}{2}\right)^2),$$

$\gamma$ is the heat capacity ratio of steam, and $\rho_o$ is the density at the inlet pressure $P_o$ and temperature.

To achieve wide coverage, multiple outlet orifices 42 may be placed adjacent to each other to attain a wider pressure profile. (See, e.g. embodiment of FIGS. 12 and 13 having a single inlet orifice 40 and two outlet orifices 42). The spacing ΔD (see FIGS. 12 and 13) between the neighboring outlet orifices 42 is preferably designed to optimize the overall performance. Spacing ΔD that is too small may not achieve desired coverage; while spacing ΔD that is too large may result in a low-pressure region between neighboring orifices 42.

Figure 6:
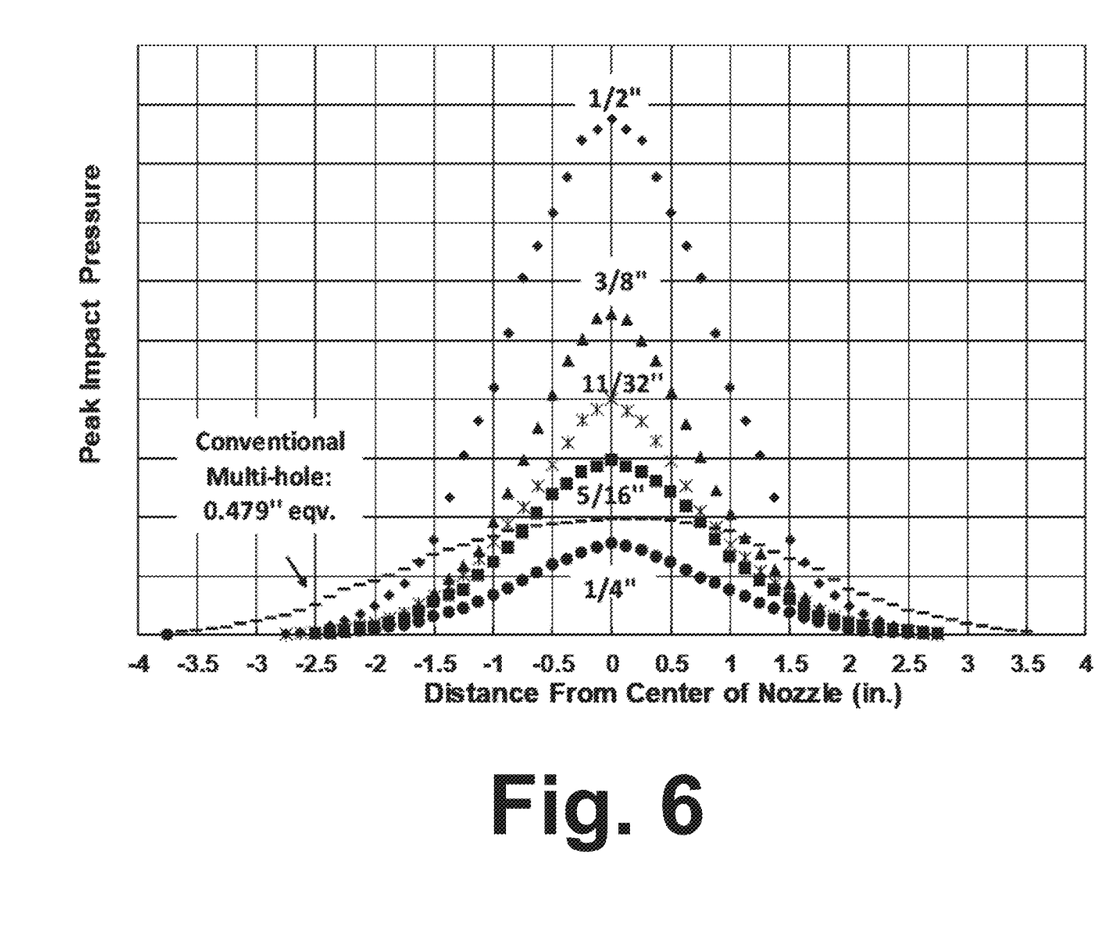

With reference to FIG. 6, velocity contours are illustrated of a single jet (FIG. 6(A)) developed from a CD nozzle with an inlet steam pressure of 150 psig based on two-dimensional asymmetric computational fluid dynamics modeling. The result shows that, for this jet, the optimum spacing between adjacent orifices should not exceed $8D_o$ (a distance that is equal to eight orifice diameters $D_o$), otherwise an undesired low-pressure region may form in the middle. Thus, a converging-diverging multi-jet nozzle design can generate a jet with both strength and coverage while minimizing steam consumption. FIG. 6(B) illustrates the velocity contours of a dual jet developed from a CD nozzle with an inlet steam pressure of 150 psig. The results show a spacing of $6D_o$ does not produce an undesired low-pressure region.

To evaluate the performance of the CD multi-jet nozzles, various design parameters were examined, while a conventional multi-hole (non-CD) nozzle was also tested for performance comparison. A summary of the experimental conditions is listed in Table 1.

TABLE 1

| Parameter | Condition |
|---|---|
| Nozzle throat diameter | ¼ to ½ inch |
| Number of outlet orifices | 1 to 3 |
| Spacing between outlet orifices | $8D_o$ to $16D_o$ |
| Inlet pressure | 100 to 150 psig |
| Distance between nozzle and pitot tube | 20 and 24 inches |

In the experimental setup used in this study, compressed air was used in the experiments to simulate steam. A pitot tube array was placed in front of the nozzle being tested to measure the jet peak impact pressure, which is an indication of shatter jet strength. The position of the pitot tube could be adjusted in the x-, y-, and z-directions. Variation of the x- and y-position generates a jet pressure profile, and the varying z-position changes the distance between the nozzle and the pitot tube.

With reference to FIG. 6, the nozzle performance is shown for five CD single-jet nozzles with different throat diameters, ¼ in., 5/16 in., 11/32 in., 3/8 in., and ½ in. FIG. 6 plots shatter jet pressure profile with different orifice sizes (distance: 20 in., pressure: 150 psig). The results show that in general, a larger orifice size resulted in a higher jet strength. The conventional multi-hole nozzle used as a reference has an equivalent orifice diameter of 0.48 in. calculated based on the total open area, which is slightly smaller than the largest CD nozzle of ½ in. It generates a wider coverage than a CD single-jet nozzle due to the larger number of orifices, but the strength is significantly less than that of a CD nozzle with a similar orifice size.

Figure 7:
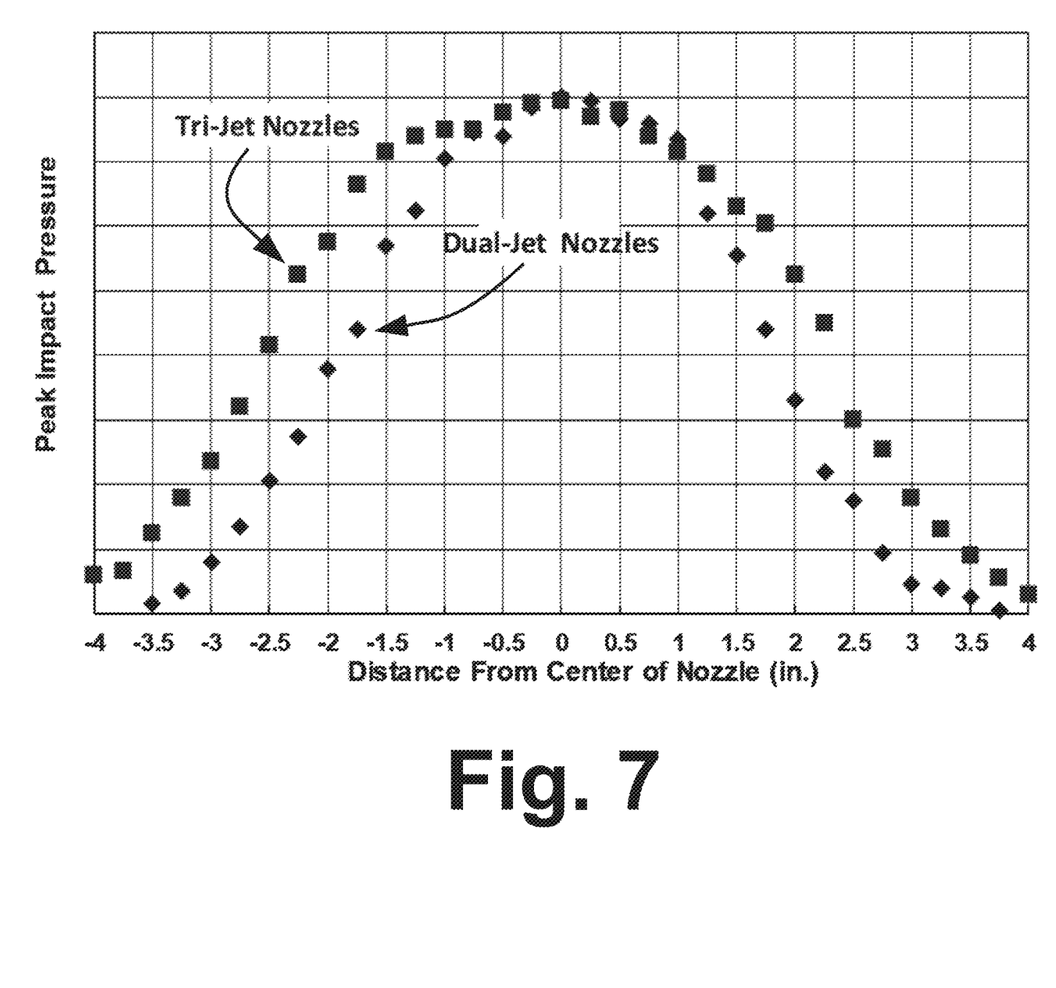
Figure 8:
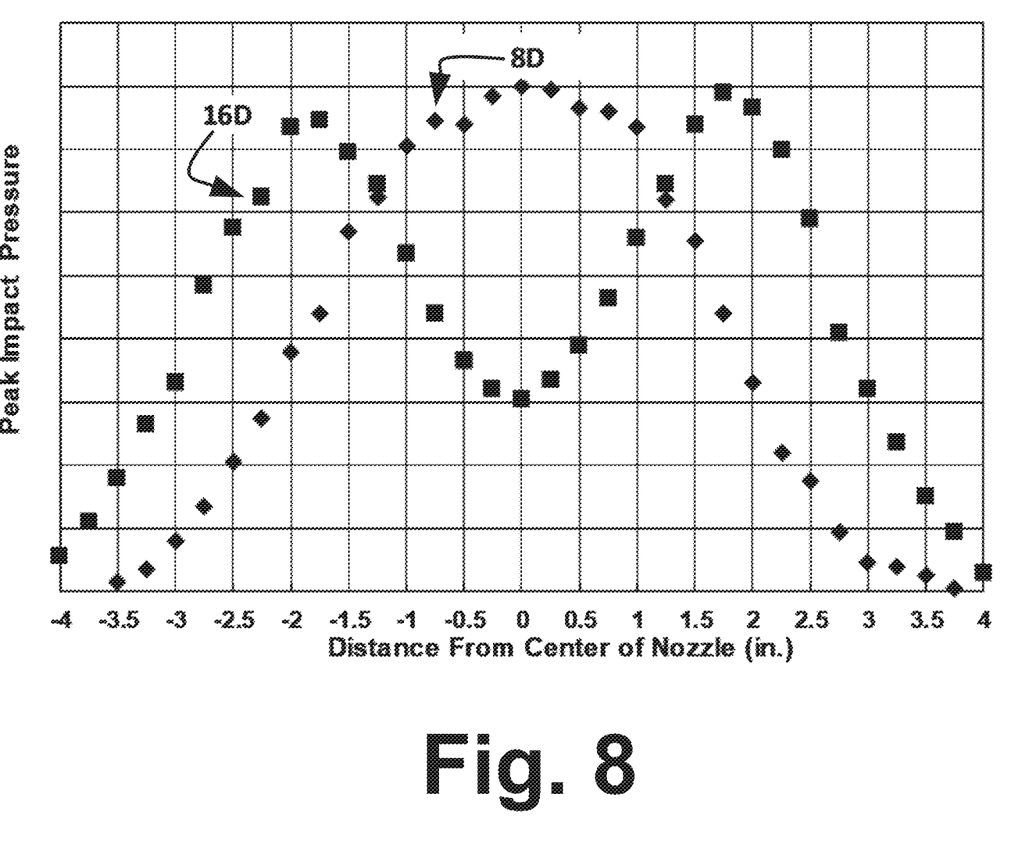

With reference to FIGS. 7 and 8, the effect of the number of nozzles and spacing between the CD orifices were also investigated. FIG. 7 shows the pressure profile for a dual-jet nozzle and a tri-jet nozzle (distance: 20 in., pressure: 150 psig), and FIG. 8 shows the pressure profile for a dual-jet nozzle with different spacings between the orifices: $8D_o$ (eight diameters) and $16D_o$. Again in FIG. 8, the distance is 20 in., and the pressure is 150 psig. The results show that increasing the number of nozzles generates a wider pressure profile with similar peak impact pressure at the centerline. When the orifices are placed too far apart, a low-pressure region in the middle is formed, which reduces the effectiveness of the shatter jet.

Figure 9:
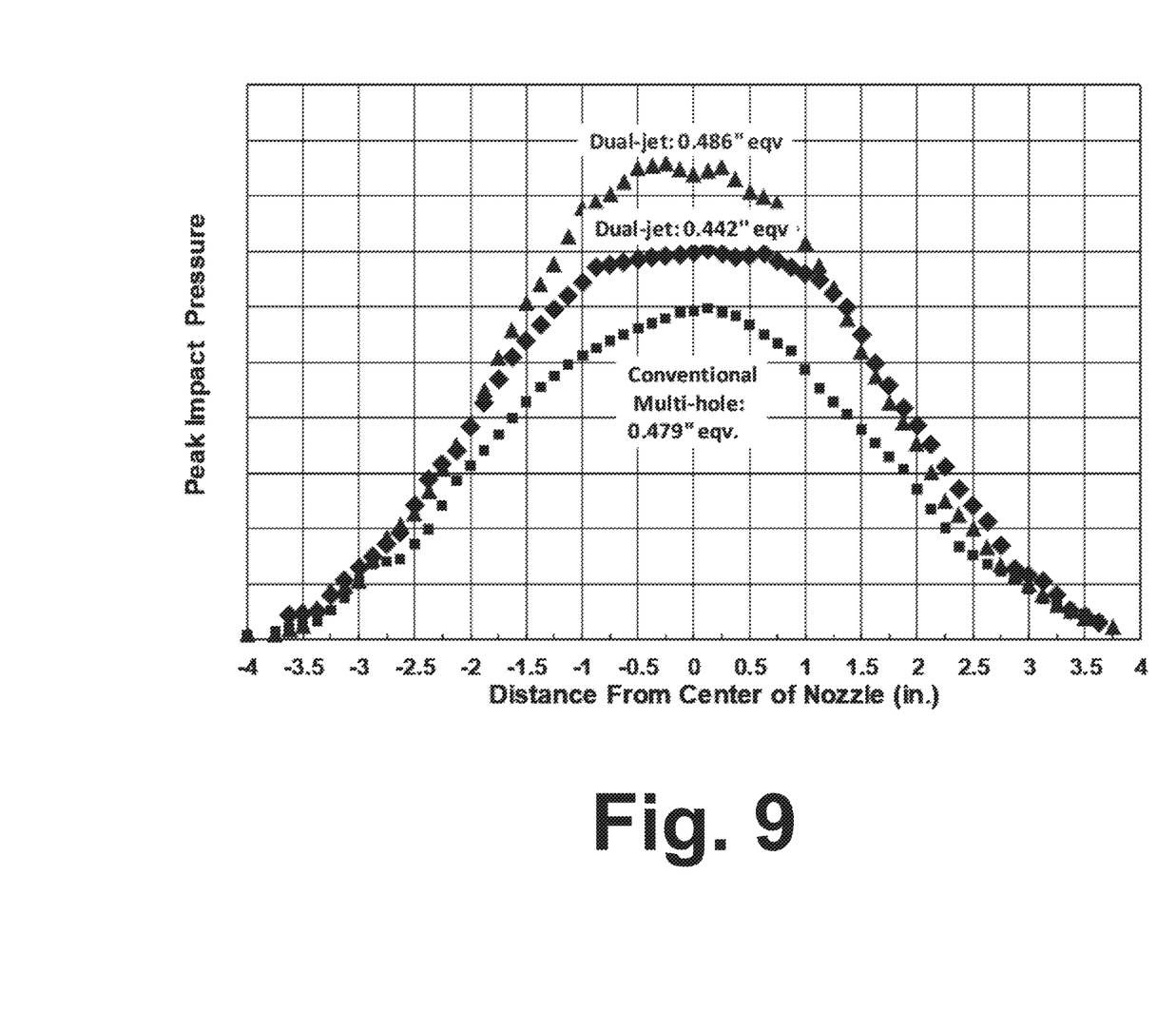

With reference to FIG. 9, the pressure profile is presented of two CD dual-jet nozzles with the same orifice spacing but different throat sizes (D), and that of a conventional multi-hole shatter jet nozzle for comparison. The result demonstrates that the converging-diverging multi-jet nozzle 20 of FIG. 4 can outperform a conventional shatter jet nozzle by achieving higher energy and wider coverage while consuming less steam. The comparison of the jet pressure profiles from optimized nozzles and the conventional nozzle presented in FIG. 9 is again for a distance of 24 in. and a pressure of 150 psig.

Figure 10:
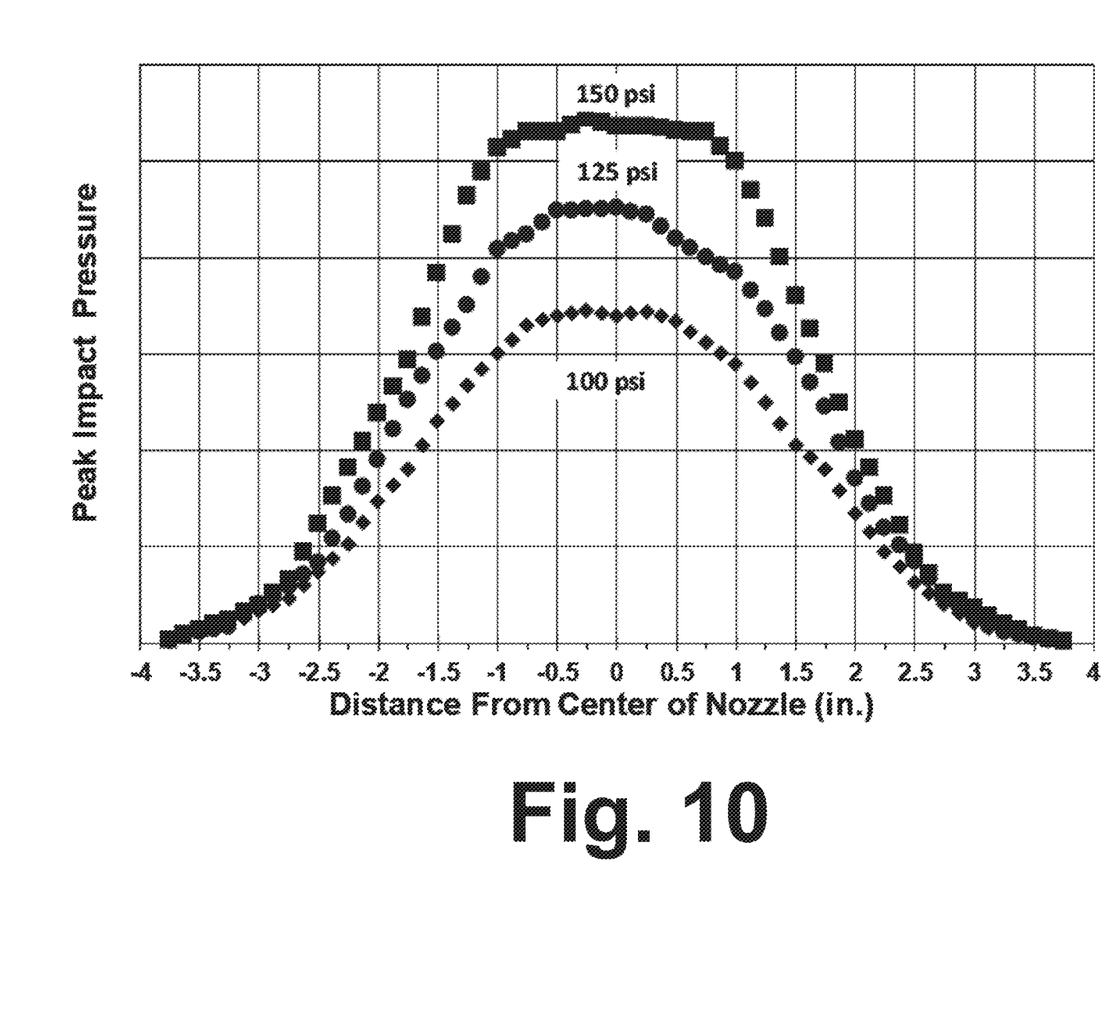
Figure 11:
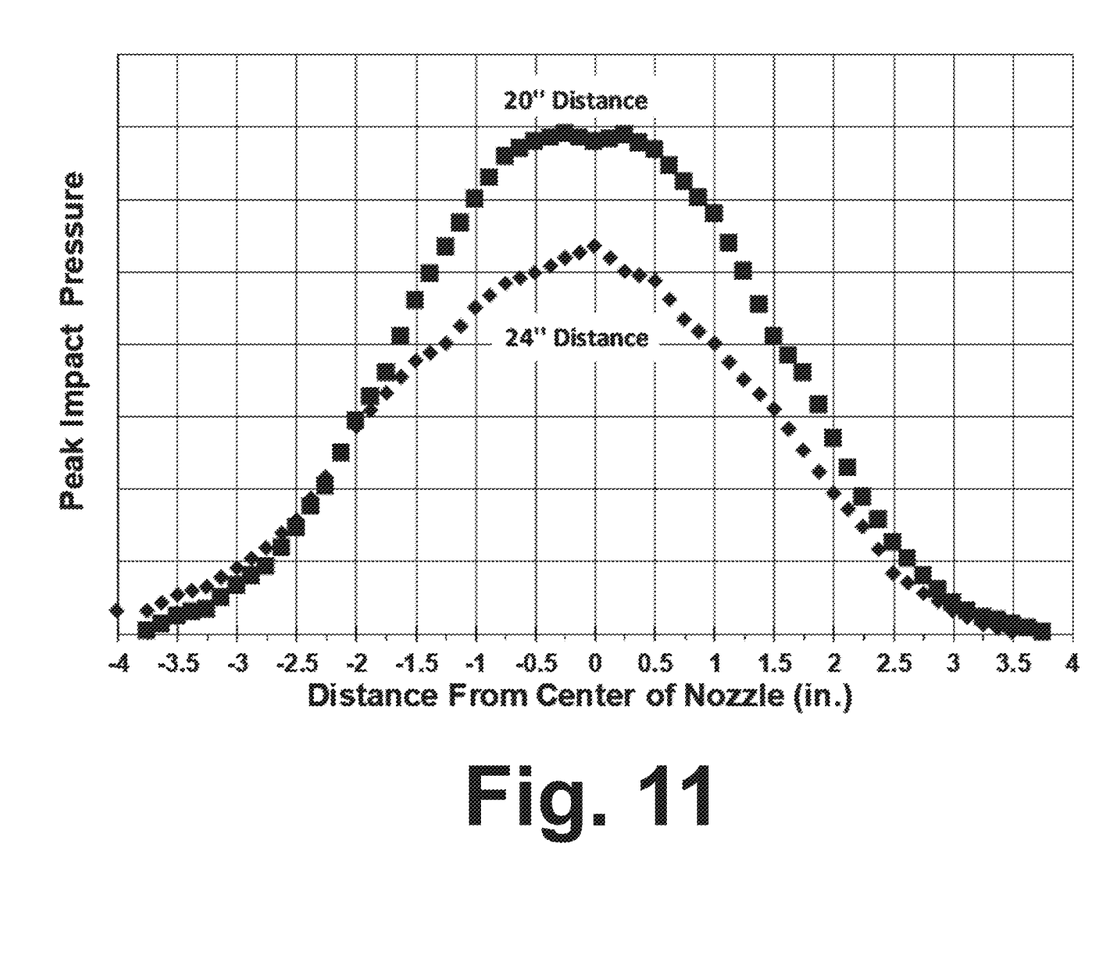

With reference to FIGS. 10 and 11, the inlet pressure and distance between the smelt stream and shatter jet can also affect the performance of a shatter jet. FIG. 10 compares the performance of CD dual-jet nozzles with different inlet pressure by plotting the shatter jet pressure profile at different steam pressures. FIG. 11 compares the performance of CD dual-jet nozzles with different distances from the pitot tube by plotting the shatter jet profile at different distances to the pitot tube. The results presented in FIGS. 10 and 11 show that the increase in pressure and decrease in distances leads to a higher jet strength and wider coverage.

In summary, the disclosed shatter jet design (e.g. as embodied by illustrative shatter jet nozzle 20 of FIG. 4) improves smelt shattering effectiveness and the safety of dissolving tank operation.

Figure 12:
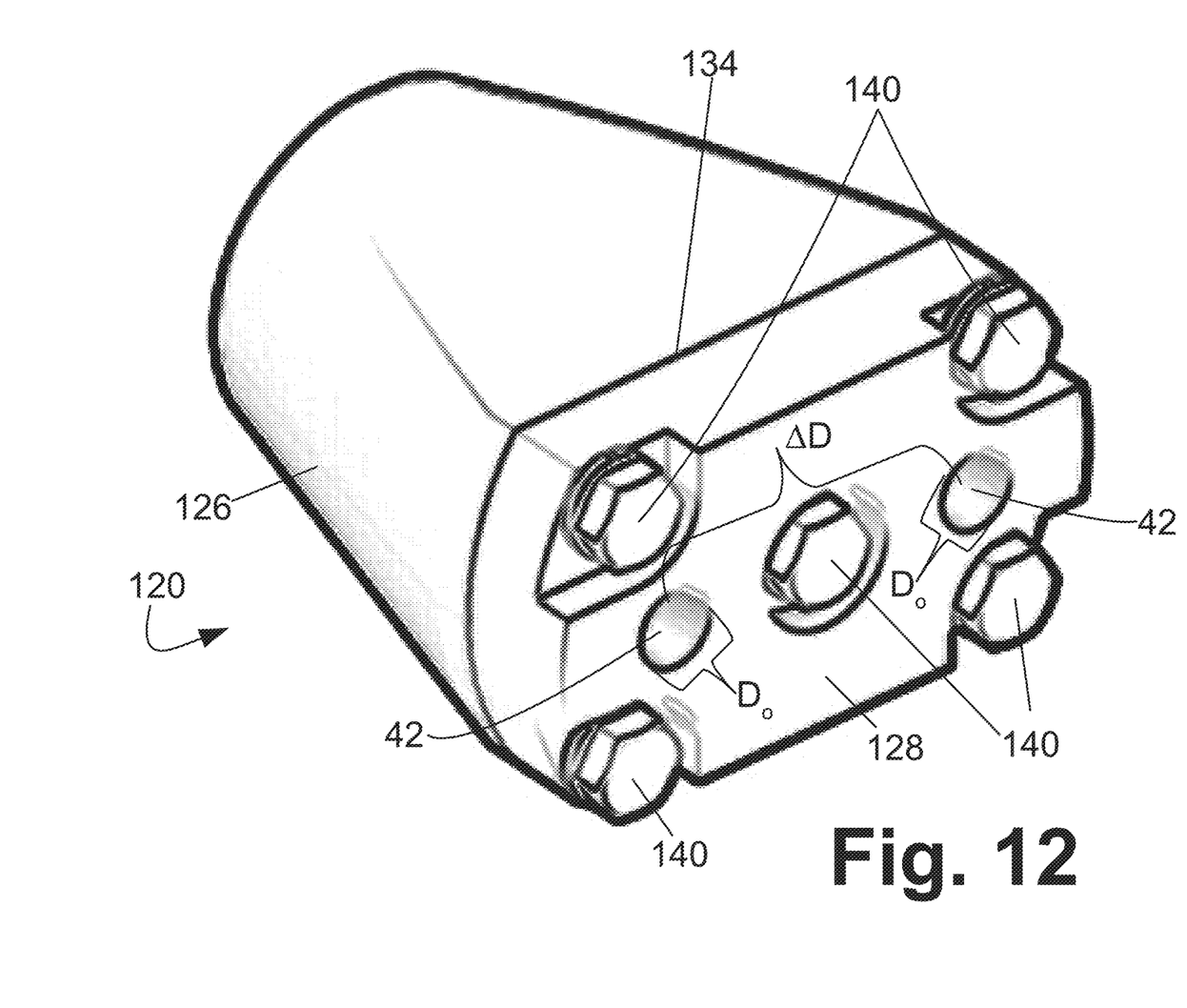
FIGS. 12 and 13 diagrammatically illustrate a smelt shattering nozzle in accordance with another embodiment in (A) perspective view and (B) sectional perspective view.
Figure 13:
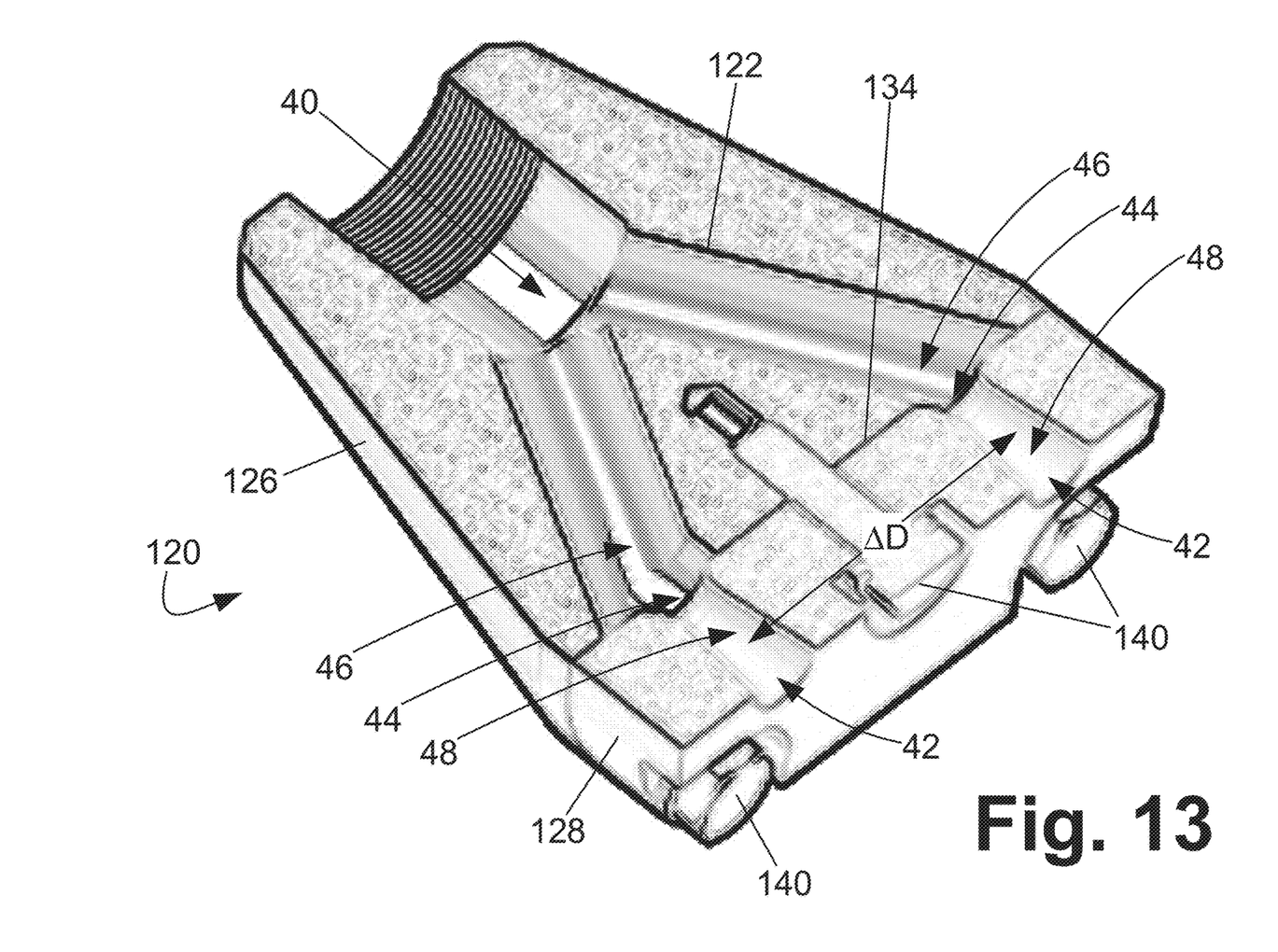

With reference now to FIGS. 12 and 13, another illustrative shatter jet nozzle 120 employing the converging diverging (CD) approach is diagrammatically illustrated. FIG. 12 shows a perspective view of the shatter jet nozzle 120, which is a dual jet design with two outlet orifices 42, while FIG. 13 shows a perspective sectional view of the shatter jet nozzle 120 revealing the internal fluidic pathway 122. In this embodiment, the nozzle comprises a first section 126 in which the convergence zone 46 is formed, and a second section 128 in which the divergence zone 48 is formed. An interface 134 at which the first section 126 and the second section 128 are joined delineates the constriction or throat 44. The two sections 126 and 128 are separate pieces that may be connected together via bolts 140 (as illustrated) or by other connection means such as clips, welds, threading, or the like. In the illustrative shatter jet nozzle 120 of FIGS. 12 and 13, the first section 126 includes the inlet orifice 40 and the second section 128 includes the outlet orifice 42 (or, in the illustrative two-jet design, two outlet orifices 42). The first section 126 and the second section 128 are secured together to define the fluidic pathway 122 between the inlet orifice 40 and each outlet orifice 42, with the fluidic pathway 122 having a "Y" branch to enable the single inlet orifice 40 to feed steam to both outlet orifices 42 as seen in the sectional view of FIG. 13. In this embodiment, the constriction or throat 44 is defined at the interface 134 between the first and second sections 126, 128. The portion of the fluidic pathway in the second section 128 (that is, the divergence zone 48) widens from the interface 134 (corresponding to the constriction or throat 44) to the outlet interface 42. As seen in FIG. 13, at the interface 134, the portion of the fluidic pathway 122 in the first section 126 (i.e., the convergence zone 46) has a larger diameter than the portion of the fluidic pathway 122 in the second section 128 (i.e., the divergence zone 48). The resulting abrupt reduction in the diameter of the fluidic pathway 122 at the interface 134 defines the constriction or throat 44.

While FIG. 13 employs a "Y" branch to feed steam to two outlet orifices 42 with the single inlet orifice 40, more generally the fluidic pathway 122 may include a 1-to-N manifold in which a single inlet orifice feeds steam to N outlet orifices.

The shatter jet nozzle 120 of FIGS. 12 and 13 permits on-site tuning via selective pairing of the convergent and/or divergent portions 126, 128 having different characteristics such as (but not limited to) number of orifices, cross sectional shape of orifices, cross section area of orifices, convergence and or divergence profile within each portion, and directional output of the outlet orifice.

Spacing geometry between outlet orifices 42 enable widening of the steam patterns while maintaining a desired impact pressure profile. In at least one embodiment the spacing ΔD between orifice outlets 42 of the dual jet nozzle 120 is $4D_o$, where $D_o$ is the diameter of the orifice outlet 42 ($D_o$ is labeled only in FIG. 12). In another embodiment the spacing ΔD is in the range of about $4D_o$ to about 16D, and more preferably between about $4D_o$ and about $8D_o$. In some embodiments, the outlet orifices may be of different sizes, e.g. a cross-sectional dimension of the first outlet orifice may be larger than a cross-section dimension of the second outlet orifice (variant not shown in FIGS. 12 and 13 which have the same $D_o$ for both outlet orifices 42 of the dual jet nozzle 120).

While the above description constitutes the preferred embodiment of the present invention, it will be appreciated that the invention is susceptible to modification, variation and change without departing from the proper scope and fair meaning of the accompanying claims.

The invention claimed is:

1. A smelt shattering apparatus comprising:
a first separable section including an inlet orifice;
a second separable section including a first outlet orifice and a second outlet orifice;
wherein:
the first separable section and the second separable section are secured together at an interface to form a fluidic pathway between the inlet orifice and each of the first outlet orifice and the second outlet orifice; and
a portion of the fluidic pathway in the first section has a larger diameter than a portion of the fluidic pathway in the second section to form a convergence divergence zone located between the inlet orifice and the first outlet orifice comprising an abrupt reduction in the diameter of the fluidic pathway at the interface between the first separable section and the second separable section.

2. The apparatus of claim 1 wherein a convergence zone of the convergence divergence zone begins in the first separable section.

3. The apparatus of any one of claims 1 and 2 wherein a divergence zone of the convergence divergence zone has a profile defined by a fluidic pathway within the second separable section.

4. The apparatus of claim 1 wherein the first outlet orifice has a cross-sectional dimension and the second outlet orifice is located a distance of between about 4 and about 10 times of the cross-sectional dimension from the first outlet orifice.

5. The apparatus of claim 1 wherein a cross-sectional dimension of the first outlet orifice is larger than a cross-section dimension of the second outlet orifice.

6. The smelt shattering apparatus of claim 1, further comprising:
bolts, clips, or threading by which the first and second separable sections are secured together.

7. A smelt shattering apparatus comprising:
a first section including a single inlet orifice; and
a second section including a first outlet orifice and a second outlet orifice;
wherein the first section and the second section are secured together to define a fluidic pathway between the inlet orifice and each of the first outlet orifice and the second outlet orifice, the fluidic pathway having a first branch connecting the single inlet orifice with the first outlet orifice and a second branch connecting the single inlet orifice with the second outlet orifice, and there being a constriction defined in each of the first branch and the second branch at an interface between the first and second sections.

8. The smelt shattering apparatus of claim 7, wherein the each of the first and second outlet orifices has a diameter and a spacing between the first outlet orifice and the second outlet orifice is less than or equal to eight times the diameter.

9. The smelt shattering apparatus of claim 7, wherein the first section and the second sections are separable.

10. The smelt shattering apparatus of claim 9, further comprising:
bolts, clips, or threading by which the first and second separable sections are secured together.

11. The smelt shattering nozzle of claim 7 wherein:
a portion of the first branch in the second section widens from the interface to the first outlet orifice; and
a portion of the second branch in the second section widens from the interface to the second outlet orifice.

12. The smelt shattering nozzle of claim 11 wherein:
at the interface, a portion of the first branch in the first section has a larger diameter than the portion of the first branch in the second section; and
at the interface, a portion of the second branch in the first section has a larger diameter than the portion of the second branch in the second section.

* * * * *